United States Patent [19]
Garyantes et al.

[11] Patent Number: 5,257,983
[45] Date of Patent: Nov. 2, 1993

[54] BLOOD BAG FOR LYOPHILIZATION

[75] Inventors: Tina K. Garyantes, Altadena; Daniel F. Jones, San Dimas; Hardin Gilbert, Pasadena; Miller Cho, La Cresencenta, all of Calif.

[73] Assignee: Cryopharm Corporation, Pasadena, Calif.

[21] Appl. No.: 685,465

[22] Filed: Apr. 12, 1991

[51] Int. Cl.$^5$ .............................................. A61B 19/00
[52] U.S. Cl. ..................................... 604/403; 383/104; 604/408
[58] Field of Search ..................... 604/403, 408–410, 604/405, 406; 383/104, 119

[56] References Cited

U.S. PATENT DOCUMENTS

| | | |
|---|---|---|
| 3,942,529 | 3/1976 | Waage . |
| 3,951,148 | 4/1976 | Herb . |
| 3,980,198 | 9/1976 | Baumgarten ................. 604/403 |
| 4,035,924 | 7/1977 | Faure . |
| 4,112,989 | 9/1978 | Grode . |
| 4,131,200 | 12/1978 | Rinfret . |
| 4,191,231 | 3/1980 | Winchell . |
| 4,198,972 | 4/1980 | Herb ........................... 604/408 |
| 4,253,458 | 3/1981 | Bacehowski . |
| 4,469,227 | 9/1984 | Faust ........................... 383/119 |
| 4,507,123 | 3/1985 | Yoshida . |
| 4,516,977 | 5/1985 | Herbert . |
| 4,619,650 | 10/1986 | Wisdom . |
| 4,670,013 | 6/1987 | Barnes . |
| 4,731,072 | 3/1988 | Aid ............................. 604/408 |
| 4,973,327 | 11/1990 | Goodrich, Jr. et al. ............. 604/408 |
| 4,994,021 | 2/1991 | Smith et al. ....................... 604/409 |

FOREIGN PATENT DOCUMENTS

343596A2 5/1989 European Pat. Off. .

Primary Examiner—Robert A. Hafer
Assistant Examiner—Sam Rimell
Attorney, Agent, or Firm—Heller, Ehrman, White & McAuliffe

[57] ABSTRACT

A lyophilization bag is provided in which a fluid, such as blood, may be introduced, lyophilized without collapsing the bag, stored, reconstituted and distributed from the bag without intermediate transfer of the useful contents from the bag.

4 Claims, 4 Drawing Sheets

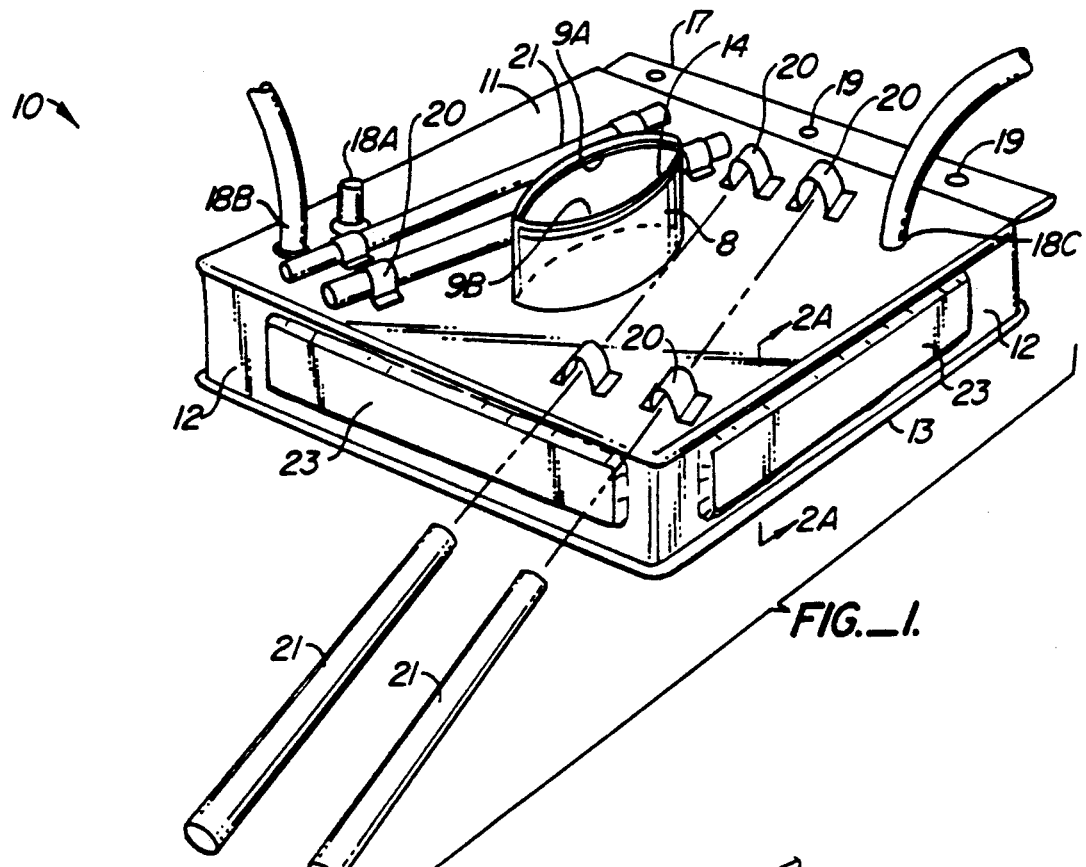
FIG._1.
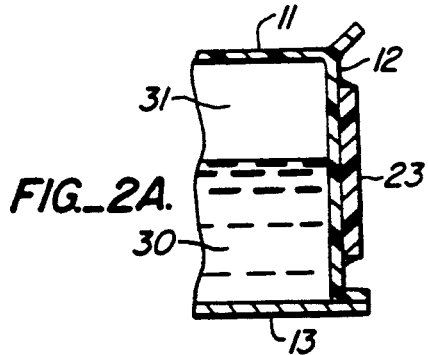
FIG._2A.
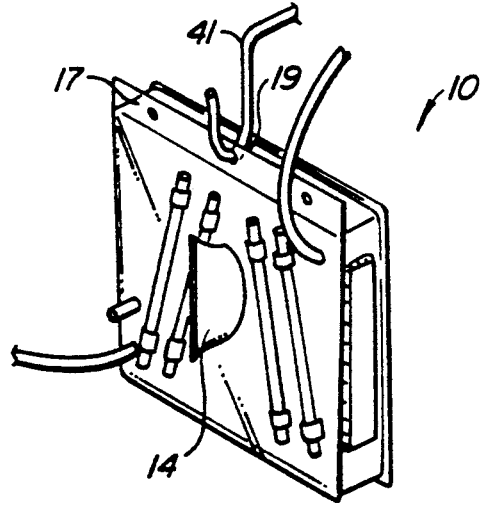
FIG._3.
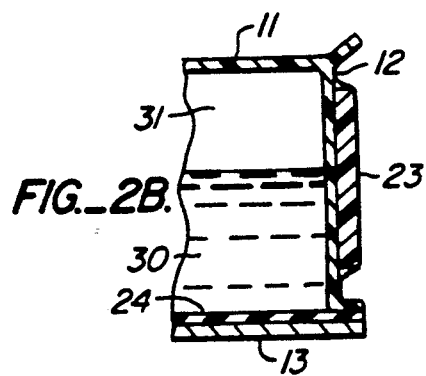
FIG._2B.

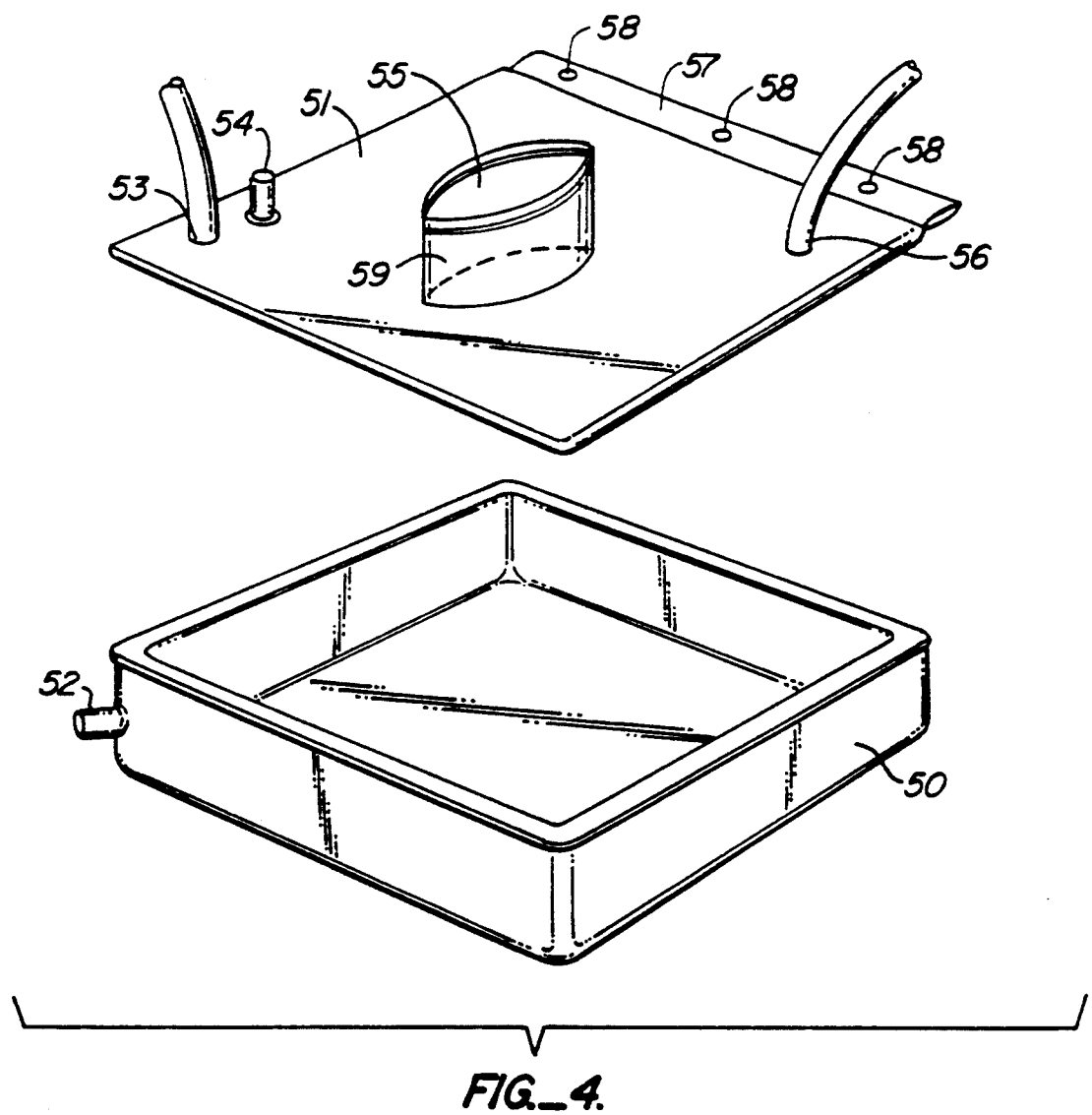
FIG._4.

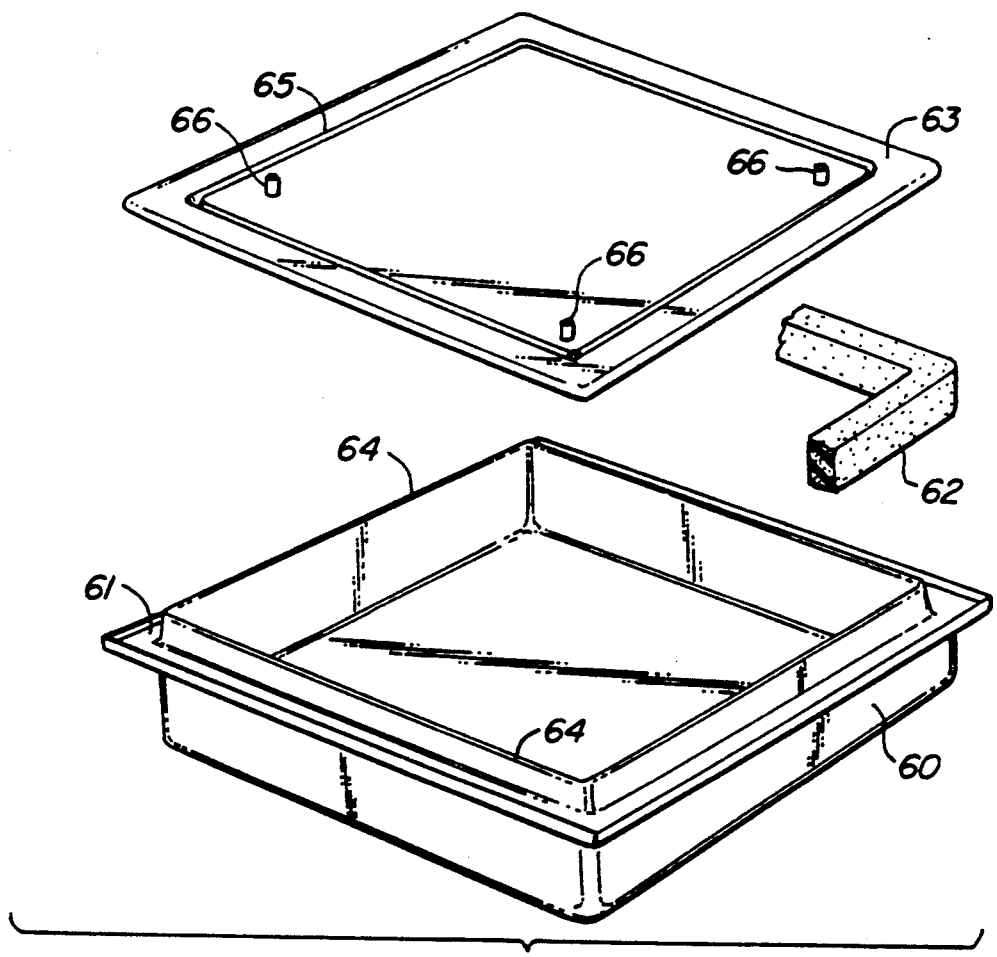
FIG._5.
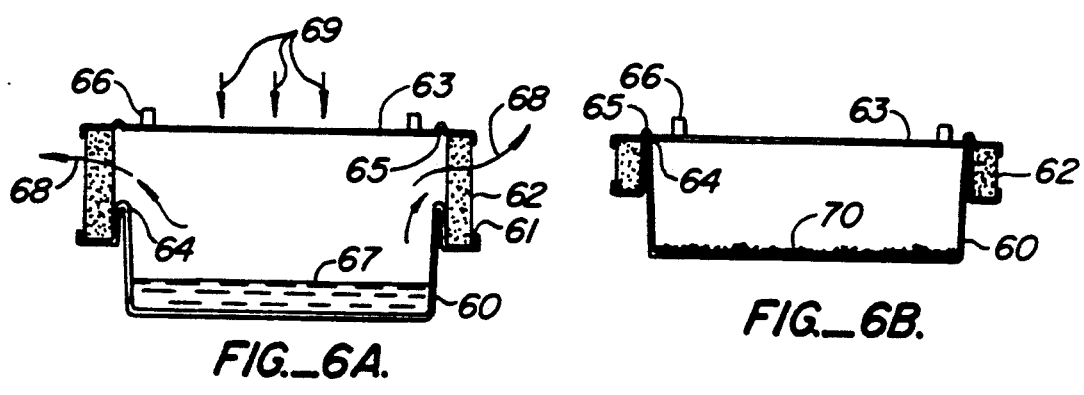
FIG._6A.
FIG._6B.

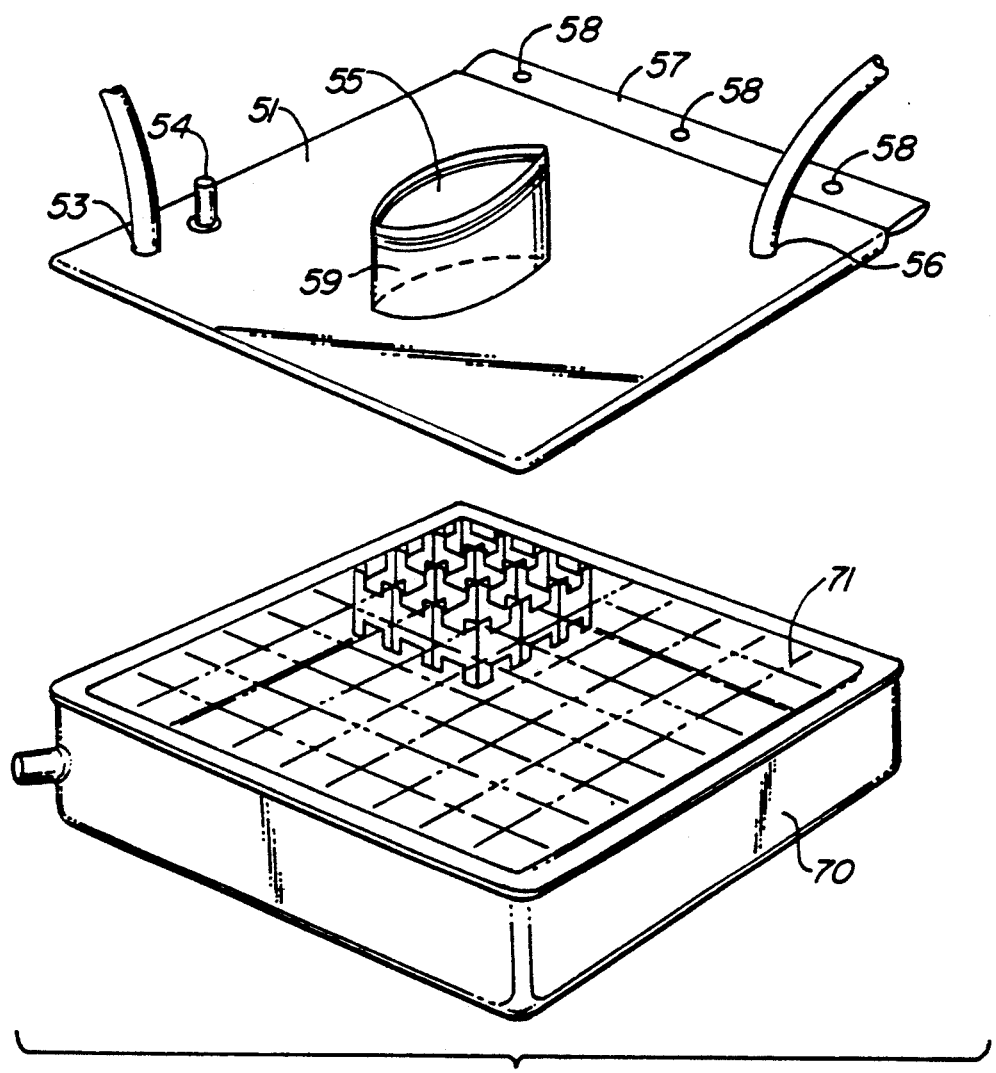
FIG._7.
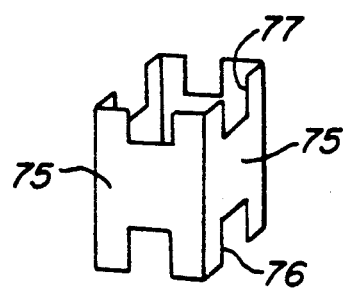
FIG._8.

BLOOD BAG FOR LYOPHILIZATION

This invention relates to a bag for use in the lyophilization (freeze-drying) of fluid, particularly blood or red blood cell suspensions for transfusion, and which can also be used for storage and reconstitution of the lyophilized product. The bag for lyophilization according to this invention can also be used for the lyophilization, storage, and reconstitution of blood substitutes, such as liposome encapsulated hemoglobin (hemosome) solutions and cell-free hemoglobin solutions; fluid blood components, including serum and fractions derived from serum; or any protein-containing solution or suspension.

BACKGROUND OF THE INVENTION

There are several practical problems which are encountered in the lyophilization, storage and reconstitution of fluid products, particularly blood. One of the objects, particularly in dealing with blood or other medical products, is to handle the blood as little as possible to minimize exposure to sources of possible contamination Furthermore, the blood should be able to be conveniently stored in its lyophilized state in a sterile environment and then reconstituted with as little handling as possible and with minimal exposure to possible sources of contamination.

There is the practical problem of conservation of storage space. It would be desirable to have the container in which the blood is stored take up the minimum amount of room, since in many instances, it is stored in a controlled temperature environment, such as a refrigerator, in which space is limited.

Another problem is that the container for the blood must not only be susceptible to sterilization, but must also mechanically withstand low temperatures, particularly, for example, temperatures as low as about $-70°$ C. used in lyophilization processes, and withstand application of a vacuum.

To minimize storage utilization, the above requirements suggest the use of a flexible, collapsible container. On the other hand, if the contents of the bag are to be lyophilized under vacuum, the bag must be able to withstand application of a vacuum without collapsing during lyophilization.

It is thus an object of the present invention to provide a lyophilization bag, which can be used during lyophilization, then used for reconstitution of the contents so that the contents may be used directly from the bag which serves as a fully-enclosed sterile container system. Thus, according to the invention, the same container may be used for lyophilization, storage and reconstitution, thus avoiding transfers of the contents for these purposes.

Other objects of the invention will be apparent from the following description and accompanying drawings and appended claims.

SUMMARY OF THE INVENTION

The present invention provides a plastic bag comprising an upper wall and a lower wall sealed to a peripheral side wall. The upper wall has a sealable major port and a plurality of sealable auxiliary ports, and the side wall has at least one sealable side port adapted with sealing means and located approximate to the upper edge of the side wall. In one embodiment, the upper wall is adapted with securing means to receive removable reinforcing members to restrain the upper wall from flexing and collapsing the bag. The lower wall is rigid. The lower wall is optionally lined on its interior with a lining which is compatible with the contents of the bag. The side wall is made of a flexible material, with reinforcing members affixed thereto. The bag is also adapted with an attachment means for suspending the bag in a position whereby at least one of the side ports is at a location for withdrawing the fluid contents from the bag.

In another embodiment, the bottom and side walls are formed as one rigid form, and the top wall, also of a rigid material, is permanently affixed thereto.

In a third embodiment a rigid lyophilization bag is provided in which the top and the body of the storage container are attached to a deformable porous spacer so that the bag can be placed within the lyophilizer and be self-sealing within the lyophilizer. In the lyophilizer the volatile liquid contents of the container are evacuated by passing through the porous spacer. The top of the container is then mechanically moved to compress the deformable spacer until a point at which the top and the body of the container seal to one another. Once sealed, the lyophilizer is vended and the container can be removed from the lyophilizer. The sealing may be accomplished, for example, by mechanically moving shelves in the lyophylizer so that each shelf compresses the tops of the bags in the next lower shelf.

In yet another embodiment, a series of partitions is provided within a container of a lyophilization bag which, while providing walls with mass transfer conduits which define compartments, still allow for free flow of vapor in the vapor space above the fluid so that the vaporized contents may be evenly evacuated and fluid contents may be evenly distributed for filling and reconstitution. A first advantage of the partitions is thay they speed the drying process. A second advantage of these partitions is that the solid remaining after lyophilization in each of the compartments forms essentially a single pellet. These pellets are more readily reconstituted than a single mass of lyophilized solid. This feature may be used in any one of the above embodiments of the container.

BRIEF DESCRIPTION OF THE DRAWING

FIG. 1 is a perspective view of one embodiment of a lyophilization bag according to the present invention.

FIG. 2A is a partial cross-section view through section line 2—2 of FIG. 1 of a side wall and side wall reinforcing member.

FIG. 2B is a partial cross-section view through section line 2—2 of FIG. 1 showing a modified lower wall having an inner lining.

FIG. 3 is a perspective view of the lyophilization bag of FIG. 1 suspended in a position for withdrawing the liquid contents therefrom through one of the side ports.

FIG. 4 is an exploded perspective view of another embodiment of the invention having rigid walls.

FIG. 5 is an exploded view showing another embodiment of the present invention having a deformable porous spacer.

FIGS. 6A and 6B are cutaway side views of the embodiment shown in FIG. 5 showing the container in an open and closed form, respectively.

FIG. 7 is an exploded view showing an embodiment wherein the container contains dividers.

FIG. 8 is a detail view of a cell within the container of FIG. 7.

DESCRIPTION OF THE PREFERRED EMBODIMENTS

Referring to FIG. 1 there is shown a bag 10 having upper wall 11 and peripheral wall 12 made of a flexible plastic material. The preferred material is a polymeric substance comprising polyvinylchloride film and a plasticizer, such as polyvinylchloride Grade 6 (made by Ellay, Inc., Commerce, Calif.). A preferred material is PVC containing diethyl hexyl phthalate (DEHP) as plasticizer. As shown, the bag 10 comprises an upper wall 11 and a rigid bottom wall 13 which are peripherally bonded at their edges to a peripheral wall 12. The bonded edges between the upper wall 11 and the peripheral wall 12 and, between the bottom wall 13 and peripheral wall 12 may be made by heat or radio frequency sealing the edges of the walls. However, any equivalent means of sealing the walls together to form the bag may be utilized. The upper wall 11 accommodates a major port 14 which, as shown, is approximately centrally located on upper wall 11. The port 14 is intended to be an evacuation port used during lyophilization. It is sealable by interlocking ridges 9A and 9B on flexible collar 8 which form an air-tight seal when the ridges are pressed together. For example, ridges 9A and 9B may be the type of seal commonly known as Zip-Loc TM seals, or it may be sealed by RF or heat. There are also side ports 18A, 18B and 18C, as shown, which are located on upper wall 11 so as to avoid plugging of these ports by any material within the bag 10 when the bag is partially filled with a liquid or other fluid substance while it rests flat on bottom wall 13 on a level surface. When bag 10 is in an upright position, as shown in FIG. 3, port 18C will be above the level of any liquid contents.

On one side of the bag 10 adjacent to port 18C is located a tab 17 which, as shown, is bonded to the upper edge of upper wall 11. Tab 17 accommodates a plurality of orifices 19 from which the bag 10 can be suspended, as further described hereinbelow in connection with FIG. 3. Since upper wall 11 and peripheral wall 12 are made of a flexible material, the bag would be collapsible under vacuum, if not reinforced. Accordingly, as shown in FIG. 1, there is shown on upper wall 11 loops 20 which are bonded to the upper wall 11 to retain reinforcing inserts 21. The reinforcing inserts 21 may be made of rigid or semi-rigid material, such as polyethylene, of sufficient strength to prevent collapsing of bag 10, and in particular, to prevent collapsing of upper wall 11 when a vacuum is applied to the interior of bag 10 by withdrawal of gas and other vapors through port 14. The inserts 21 need only be of sufficient strength to prevent the collapse of wall 11 when vacuum pressures normally used in lyophilization processes are applied within the bag 10.

Similarly, to prevent inward collapse of peripheral wall 12 rigid reinforcing members 23 are affixed (by heat-bonding bonding, adhesives, etc.) to the peripheral wall 12. The reinforcing members 23 may be made of the same rigid or semi-rigid polyethylene material as inserts 21 Members 23 are not co-extensive with the respective walls to which they are affixed to allow folding of the flexible walls to conserve space when the bag 10 is empty.

The bottom wall 13 of bag 10 is made of a rigid material, preferably the same material as used to form inserts 21 and reinforcing members 23.

Any of the ports 16, 18A, 18B, 18C or 14 may be sealed until use.

Referring to FIG. 2A there is shown a partial cut-away detail of peripheral wall 12, reinforcing member 23 along line 2—2 of FIG. 1. As shown in FIG. 2A, the wall 12 is supported from collapsing inwardly by reinforcing member 23 which is affixed thereto. Preferably, the bag is not filled to its fullest extent so that the liquid or other contents 30 of the bag leave an airspace 31 within the bag so as not to plug port 16 when the bag is lying flat on bottom wall 13.

Referring to FIG. 2B, there is shown in partial cut-away detail, a modification of bag 10, taken along line 2—2 of FIG. 1. In this modification, there is a liner 24 next to the inner surface of lower wall 13. The liner 24 may be interfacially affixed to wall 13 (glue, thermal welding, etc.) or may be attached at its edges to peripheral wall 12 and lower wall 13. This embodiment is desirable if the material of which lower wall 13 is made is not compatible or not approved for contact with the contents of the bag. Liner 24 will thus serve as the contacting surface with the contents, and may be made if the same material as walls 11 and 12.

Referring to FIG. 3, there is shown use of bag 10 subsequent to reconstitution of its contents (preferably lyophilized blood or red blood cells), whereby the liquid contents may be drained through the port 16. Bag 10 is suspended from hook 41 through one of the orifices 19 in tab 17. Port 14 is shown in its sealed configuration.

Referring to FIG. 4, there is shown yet another embodiment of a lyophilization bag according to the invention. In this embodiment the bottom and peripheral walls of the bag consist of a single rigid dish 50. The top wall 51 consists of a rigid piece, affixed at its edges to the dish 50 to define the interior of the bag. Ports 52, 53, 54, 55 and 56 serve functions similar to ports 16, 18A, 18B, 14 and 18C, respectively, as described in connection with FIG. 1. An extension of wall 51 provides a tab 57, having orifices 58, which serve the same function as tab 17 and orifices 19, respectively, as described in connection with FIG. 1. The collar 59 on port 55 is flexible and is sealable as is described in connection with collar 8 in FIG. 1.

In the preferred method of using bag 10, referring to FIG. 1, after inserting the reinforcing inserts 21, major port 14 is unsealed and optionally adapted with a sterile filter (not shown in FIG. 1). One of the ports 18A, 18B or 18C is then unsealed and affixed with a conduit for filling the bag with its liquid contents to be lyophilized. Hereinafter the contents will be described as being blood.

The bag 10 is filled to a level, preferably, but not necessarily below port 16, then the filling port is resealed or the conduit thereto (not shown) is closed by an appropriate valve (not shown) or other means.

The entire bag 10 is then placed within a lyophilizer, and the contents are frozen and lyophilized. The vapor is removed through port 14 (unsealed). The bag is prevented from collapsing by the reinforcing inserts 21 and members 23, as well as rigid wall 13. Upon completion of lyophilization, the vacuum in the lyophilizer is released by venting with sterile, dry inert gas such as nitrogen. The vacuum inside the bag is thereby replaced with inert gas. The bag is then removed from the lyophilizer and all ports, or tubing attached thereto, are sealed. This creates a fully sealed sterile environment for storage of the dry product in the closed bag under a dry inert gas. If desired, the inserts 21 may be removed.

The bag and its lyophilized contents may then be stored under a range of temperatures, from −80° C. to +25° C. (room temperature), and even in excess of normal room temperatures.

When the contents of the bag are to be reconstituted, ports 18A, 18B and/or 18C may be unsealed and used for introduction and withdrawal of appropriate sterile reconstitution fluids. To use the reconstituted fluids in the bag, the bag is suspended, preferably as shown in FIG. 3, and its contents are withdrawn through port 16.

It should be apparent in the Figures that while several side ports are shown, the bag may be manufactured with as many ports as desired.

A particular advantage of the bag according to FIG. 1 of the present invention is that it conserves space before use since it may be collapsed to virtually a flat piece. The bags in FIGS. 1 and 4 are advantageous in that they may be filled, used in a lyophilizer, stored, used for reconstitution, and then drained of their contents, without ever transferring the desirable contents (blood cells) from the bag. The contents of the bag may comprise blood, protein-containing solutions, red blood cells for transfusion, serum, blood protein fractions or other components prepared from whole blood.

It will also be realized that means other than those shown may be utilized to suspend the bag, such as by loops, hooks, etc.

It will also be realized that after lyophilization is complete the bag is sealed to create a self-contained environment suitable for storage of the dried contents.

Referring to FIG. 5 there is shown another embodiment of a lyophilization bag according to the present invention. In this embodiment, the bottom and peripheral walls of the bag consist of a single rigid container body 60. A trough 61 surrounds the upper portion of the peripheral wall of container body 60. In the exploded view of FIG. 5, a deformable porous spacer 62 is accommodated by the trough 61. The peripheral portion of the lower surface of the lid 63 to the container also accommodates the top portion of the spacer 62. The upper lip 64 is adapted to securely mate with the groove 65 in the lid 63 to seal the interior of the container. Ports 66 are provided in the lid 63 for adding or withdrawing fluids.

Referring to FIG. 6A there is shown a cutaway side view of the container in FIG. 5 shown in open position. In use, one or more of the ports 66 will be used to fill the container 60 with a fluid 67 to be lyophilized. The port 66 which is used, will preferably then be resealed and the entire container is placed into the lyophilizer. When the vacuum is applied within the lyophilizer the vapors from the fluid 67 which are withdrawn from the container exit through the porous spacer 62 in a manner shown by arrows 68. The lid 63 may then be sealed onto upper surface 64 by mechanical means, such as, by lowering the upper shelf (not shown) in the lyophilizer onto lid 63.

Referring to FIG. 6B there is shown a side cutaway view of the container from FIG. 6A in a closed position. Upon completion of the lyophilization the fluid contents are converted to a solid lyophilized product 70 and the upper surface 64 of the container body 60 is securely mated with the groove 65 in the lid 63. For example, the shelves (not shown) in the lyophilizer may be remotely controlled to be mechanically lowered (or raised) to apply force to the lid(s) of containers on an adjacent shelf. The porous spacer 62 is held in a compressed configuration, so the lid 63, must be sealed with the container body 60 so that the container does not reopen under the compressive strain of the spacer 62.

Preferably, the spacer 62 will be made of a foam material or sponge and the lid 63 and container body 60 will be made of suitable rigid polymeric materials as described in connection with FIG. 1.

Referring to FIG. 7, there is shown a modification of the container shown in FIG. 4 wherein the container body 70 accommodates a plurality of dividing strips 71 which divides the interior of the container into a plurality of open ended cells.

The detail of one such cell is shown in FIG. 8. Each of the side walls 75 of the cell (except for the cells in which one or more sides are formed by the inner walls of the container body 70) have cutouts 77, 76 in the upper and lower portion, respectively, of each wall 75 so that the liquid and vapors within each cell are not isolated from the adjacent cells, therefore allowing for uniform evacuation of the vapors from the container. Particular advantages of having the fluid to be lyophilized divided into cells are that the dividers break up the "cake" of solid to accelerate the drying process and the resulting solid lyophilized product comprises pellets in the cells, thereby making it easier to reconstitute as compared to a single solid cake. The strips 71 which form the cells within the container 70 may be made of flexible strips which interconnect with one another through slots (not shown) for ready assembly. Alternatively, the entire honeycomb structure forming the cells may be formed by molding, for example, as a single piece.

What is claimed is:

1. A rigid container for containing liquid contents during lyophilization thereof and for retaining the resulting lyophilized product therein under subatmospheric pressure subsequent to lyophilization, said container comprising:

a lower container body comprising a lower wall in a continuous peripheral side wall;

containing means located adjacent to the upper edge of said side wall and exterior to said container body, said container means accommodating a deformable porous spacer and a rigid cover for said container body, said rigid cover adapted with means to slidably attach to said upper edge and seal said container;

wherein the upper surface of said spacer is in contact with said cover in a manner to retain said cover above said container body whereby exertion of a sufficient downward force upon said cover compresses said spacer and allows said cover to securely attach to said upper edge and seal said container, whereby said compressed spacer is prevented from contact with the contents within the sealed container; and at least one sealable port in said cover or in said lower container body.

2. A container according to claim 1 further comprising a plurality of dividing means, said dividing means dividing the interior of said container such that the fluid contents are distributed in a plurality of interconnecting compartments defined by said dividing means whereby the fluid contents and vapor contents in each of said compartments communicates with the fluid and vapor contents of adjacent compartments; said dividing means further providing upon drying of any fluid contents to divide the resultant lyophilized solid product into a plurality of pieces.

3. A container according to claim 1 wherein said means on said cover to securely attach to said upper edge of said container body comprises a slot of width and depth sufficient to slidably receive said upper edge and seal said container.

4. A method for lyophilizing a fluid product comprising the steps of:
   (a) introducing a product to be dried into a container according to claim 1;
   (b) introducing said container into a vacuum whereby vapors are withdrawn from said container through said porous spacer, whereby as the pressure within said container is reduced, a differential in pressure from the exterior of the container causes said cover to compress said spacer until said cover securely attaches and seals to the upper edge of said peripheral wall, thereby enclosing said container; and
   (c) exposing said container to atmospheric pressure whereby said container is maintained in a sealed condition by the pressure differential between the vacuum within said container and atmospheric pressure exterior to said container.

* * * * *

UNITED STATES PATENT AND TRADEMARK OFFICE
CERTIFICATE OF CORRECTION

PATENT NO. : 5,257,983
DATED : November 2, 1993
INVENTOR(S) : Garyantes et al

It is certified that error appears in the above-indentified patent and that said Letters Patent is hereby corrected as shown below:

Column 1, line 24, after "contamination" add --.--
Column 3, line 62, after "21" add --.--

Signed and Sealed this

Twenty-first Day of March, 1995

Attest:

BRUCE LEHMAN

Attesting Officer       Commissioner of Patents and Trademarks